United States Patent [19]

Colonno et al.

[11] Patent Number: 4,845,195

[45] Date of Patent: Jul. 4, 1989

[54] INHIBITOR OF RIBONUCLEOTIDE REDUCTASE

[75] Inventors: Richard Colonno, New Britain Township, Bucks County; Victor M. Garsky, Blue Bell, both of Pa.; John Hannah, Matawan, N.J.; Robert B. Stein, Rydal, Pa.; Richard L. Tolman, Warren, N.J.

[73] Assignee: Merck & Co., Inc., Rahway, N.J.

[21] Appl. No.: 53,179

[22] Filed: May 22, 1987

[51] Int. Cl.[4] .................. C07K 7/06; C12N 9/99; A61K 37/02

[52] U.S. Cl. .................. 530/330; 530/324; 530/325; 530/326; 530/327; 530/328; 530/329; 514/15; 514/17; 514/14; 514/16; 435/184

[58] Field of Search ................ 530/324–328, 530/329–330; 514/15, 17, 14, 16; 435/184

[56] References Cited

FOREIGN PATENT DOCUMENTS 2185024A 7/1987 United Kingdom .

OTHER PUBLICATIONS

Dutia et al., "Specific Inhibition of Herpesvirus ribonucleotide reductase by synthetic Peptides", Nature, vol. 321, pp. 439–441 (1986).

Cohen et al., "Specific Inhibition of Herpesvirus ribonucleotide reductase by a Nonapeptide Derived from the Carboxy terminus of Subunit 2", Nature, vol. 321, pp. 441–443 (1986).

Gaudreau et al., "Structure Activity Studies on Synthetic Peptides Inhibiting Herpes Simplex Virus ribonucleotide reductase", J. Biol. Chem., vol. 262, #26, pp. 12413–12416 (1987).

*Primary Examiner*—Margaret Moskowitz
*Assistant Examiner*—Abdel A. Mohamed
*Attorney, Agent, or Firm*—Frank S. Chow; Donald J. Perrella; Hesna J. Pfeiffer

[57] ABSTRACT

The pentapeptide Val Val Asn Asp Leu has been found to be the shortest peptide sequence that inhibits the activity of the ribonucleotide reductase enzyme of herpes simplex virus in vitro thereby inhibiting viral replication. Longer peptides containing the foregoing pentapeptide sequence are more potent inhibitors.

3 Claims, No Drawings

INHIBITOR OF RIBONUCLEOTIDE REDUCTASE

BACKGROUND OF THE INVENTION

The ribonucleotide reductas enzyme of herpes simplex virus consists of 2 components which must remain associated for the enzyme to convert ribonucleotide diphosphates to deoxy ribonucleotide diphosphates. The enzyme is known to be required for herpes simplex virus replication. Dutia et al. Nature 321:439–441 (1986) and Cohen et al., Nature 321:441–443 (1986) both disclosed that the nonapeptide, Tyr Ala Gly Ala Val Val Asn Asp Leu, inhibited in vitro the activity of this enzyme. In addition Dutia et al., op. cit., also disclosed that its 8-desalanine homolog, Tyr GVly Ala Val Val Asn Asp Leu, also inhibited invitro the activity of this enzyme.

OBJECTS OF THE INVENTION

It is an object of the present invention to provide novel peptides which inhibit the activity of the ribonucleotide reductase enzyme of herpes simplex virus. Another object is to provide inhibitory peptides that are shorter than known peptides that inhibit this conversion. A further object is to provide novel longer peptides that inhibit the ribonucleotide reductase enzyme of herpes simplex virus. These and other objects of the present invention will be apparent from the following description.

SUMMARY OF THE INVENTION

The pentapeptide Val Val Asn Asp Leu has been found to be the shortest peptide sequence that inhibits the activity of the ribonucleotide reductase enzyme of herpes simplex virus in vitro. Longer peptides containing the foregoing pentapeptide sequence are more potent inhibitors.

DETAILED DESCRIPTION

It has now been found that a pentapeptide having the amino acid sequence Val Val Asn Asp Leu is the shortest peptide which is effective to inhibit the activity of the ribonucleotide reductase enzyme of herpes simplex virus in vitro. This enzyme is required for replication of the herpes simplex virus. It has also been found that longer peptides containing the foregoing amino acid sequence also are effective to inhibit the activity of this enzyme. Such other peptides are: VVNDL, NPrVVNDL, AVVNDL, AcAVVNDL, GAVVNDL, AcGAVVNDL, AGAVVNDL, YAGAVVNDL, AcYAGAVVNDL, YAGAVVNDL-NH$_2$, desNH2-YAGAVVNDL, AcYAGAVVNDL, dI-YAGAVVNDL, AcdI-YAGAVVNDL, SYAGAVVNDL, TSYAGAVVNDL, STSYAGAVVNDL, FPLSLMSTDKHTNFFECRSTSYAGAVVNDL.

The polypeptides of the present invention and the amides and salts thereof can be manufactured according to known synthetic methods elongating the peptide chain, i.e. by condensing amino acids stepwise or coupling the fragments consisting of two to several amino acids, or by combination of both processes, or by solid phase synthesis according to the method originally described by Merrifield, J. Am. Chem. Soc. 85:2149–2154 (1963). Alternatively, the peptides of the present invention may be synthesized using automated peptide synthesizing equipment.

The condensation between two amino acids, or an amino acid and a peptide, or a peptide and a peptide can be carried out according to the usual condensatin methods such as azide method, mixed acid anhydride method, DCC (dicyclohexylcarbodiimide) method, active ester method (p-nitrophenyl ester method, N-hydroxysuccinic acid imido ester method, cyanomethyl ester method, etc), Woodward reagent K method, carbonyldiimidazol method, oxidation-reduction method. These condensation reactions may be done in either liquid phase or solid phase. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

As is usual in peptide synthesis, it is necessary to protect/deprotect the $\alpha$- and $\omega$- side chain amino groups and the carboxy group of the amino acid as occasion demands. The applicable protective groups to amino groups are exemplified such as benzyloxycarbonyl (hereinafter abbreviated as Z), o-chlorobenzyloxycarbonyl [Z(2-Cl)], p-nitrobenzyloxycarbonyl [Z(NO$_2$)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified, for example, benzyl ester (OBzl), 4-nitrobenzyl ester [OBzl(NO$_2$)], t-butyl ester (OBut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenylsulfonyl (Mts), and the like. The thiol group in cysteine may be protected with benzyl, p-methoxybenzyl, triphenylmethyl, acetylaminomethyl, ethylcarbamoyl, 4-methylbenzyl, 2.4,6-trimethylbenzyl (Tmb) etc, and the hydroxyl group in serine can be protected with benzyl, t-butyl, acetyl, tetrahydropyranyl etc.

Conventional methods of peptide synthesis as described, for example, by Schroder et al., "The Peptides", Vol. I Academic Press, 1965, or Bodanszky et al., "Peptide Synthesis", Interscience Publishers, 1966 or McOmie (ed.), "Protective Groups in Organic Chemistry", Plenum Press, 1973, or "The Peptides: Analysis Synthesis, Biology", 2 Chapter 1, by Barany et al., Academic Press, 1980, the disclosures of which are hereby incorporated by reference. In the present invention the amino acids listed below are identified both by conventional 3 letter and single letter abbreviations as indicated below:

| | | |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tyrosine | Tyr | Y |
| Valine | Val | V |

EXAMPLE

Preparation of Herpes Simplex Virus Ribonucleotide Reductase

HSV RR was purified from Baby Hamster Kidney cells that were cultured with HSV2 Strain 186. After infection, cells were harvested and lysed. Crude HSV RR was prepared as described by Huszar et al., J. Virol. 37:580–588 (1981), then subjected to further purification by hydroxyapatite column chromatography. The resultant enzyme preparation was about 80% pure HSV RR as judged by SDS polyacrylamide electrophoresis.

Assay of Inhibition of HSV RR Activity

HSV RR activity was determined as the ability of the enzyme to catalyze the reduction of tritiated cytidinediphosphate to deoxyribo-cytidinediphosphate in 30 minutes at 37°C. in the presence of dithiothreitol and $MgCl_2$. Activity of oligopeptide inhibitors was determined by adding them to the reaction mix at the beginning of the incubation. Enzyme was not preincubated with inhibitor.

Synthesis, Purification, and Analysis of Oligopeptides

Oligopeptides were synthesized by either the solid phase method of Merrifield, op. cit., or by FMOC chemistry (John Morrow Stewart and Janis Dillaha Young, "Solid Phase Peptide Synthesis," 2nd ed., 1984, Pierce Chemical Co., Rockford, Ill.) and purified to >98% homogeneity by reverse phase HPLC and recovered by lyophilization as trifluoroacetic acid salts. These were analyzed for amino acid composition and in some cases sequenced. Dry peptides were resuspended in 100 mM HEPES (pH 8.0) at about 2mM, relyophilized, and stored in aliquots at −80° C. Immediately prior to use they were rehydrated with distilled $H_2O$ and centrifuged to remove any undissolved peptide. The concentrations of these stock solutions were then determined by measuring A291 nm at basic pH ($\epsilon=2.55$) for tyrosine-containing peptides and by quantitative amino acid composition for those peptides without tyrosine.

The following oligopeptides were tested for ability to inhibit herpesvirus ribonucleotide reductase according to the foregoing method and the extent of the inhibition ($\mu M$ concentration of peptide producing 50% inhibition of enzyme activity) is shown in the following table.

| Peptide | $IC_{50}(\mu M)$ |
|---|---|
| VVNDL | 250 |
| NPrVVNDL | 120 |
| AVVNDL | 51 |
| AcAVVNDL | 87 |
| GAVVNDL | 70 |
| AcGAVVNDL | 75 |
| AGAVVNDL | 80 |
| YAGAVVNDL | 10 |
| YAGAVVNDL—$NH_2$ | 75 |
| desNH2—YAGAVVNDL | 20 |
| AcYAGAVVNDL | 5 |
| dI-YAGAVVNDL | 20 |
| AcdI—YAGAVVNDL | 16 |
| SYAGAVVNDL | 17 |
| TSYAGAVVNDL | 17 |
| STSYAGAVVNDL | 17 |
| FPLSLMSTDK-HTNFFECRST-SYAGAVVNDL | 8 |

What is claimed is:

1. A peptide having the amino acid sequence selected from the group consisting of
   Val Val Asn Asp Leu,
   NPr-Val Val Asn Asp Leu,
   AcAla Val Val Asn Asp Leu,
   Gly Ala Val Val Asn Asp Leu,
   AcGly Ala Val Val Asn Asp Leu,
   Ala Gly Ala Val Val Asn Asp Leu,
   Tyr Ala Gly Ala Val Val Asn Asp Leu-$NH_2$
   desNH2Tyr Ala Gly Ala Val Val Asn Asp Leu,
   AcTyr Ala Gly Ala Val Val Asn Asp Leu,
   dI-Tyr Ala Gly Ala Val Val Asn Asp Leu,
   Ac-dI-Tyr Ala Gly Ala Val Val Asn Asp Leu,
   Ser Tyr Ala Gly Ala Val Val Asn Asp Leu,
   Ser Thr Ser Tyr Ala Gly Ala Val Val Asn Asp Leu, and
   Phe Pro Leu Ser Leu Met Ser Thr Asp Lys His Thr Asn Phe Phe Glu Cys Arg Ser Thr Ser Tyr Ala Gly Ala Val Val Asn Asp Leu, and the amides and physiologically acceptable salts thereof.

2. A composition containing a peptide of claim 1 in a pharmaceutically acceptable carrier.

3. A method of inhibiting a ribonucleotide reductase enzyme of herpes simplex virus in vitro comprising contacting the enzyme with a peptide of claim 1 for a time and under conditions sufficient to inhibit the ability of the enzyme to catalyze the reduction of ribonucleotide diphosphates to deoxy-ribonucleotide diphosphates.

* * * * *